United States Patent [19]
Larsen et al.

[11] Patent Number: 5,095,757
[45] Date of Patent: Mar. 17, 1992

[54] SPECIMEN GRIP WITH REMOTE ACTUATION

[75] Inventors: Carl G. Larsen, Minneapolis; Todd L. Wallenfelt, St. Paul, both of Minn.

[73] Assignee: MTS Systems Corporation, Eden Prairie, Minn.

[21] Appl. No.: 650,071

[22] Filed: Feb. 4, 1991

[51] Int. Cl.$^5$ .............................................. G01N 3/04
[52] U.S. Cl. ...................................................... 73/857
[58] Field of Search ............... 73/855, 856, 857, 859, 73/860; 374/46, 47, 48, 49, 50, 51

[56] References Cited

U.S. PATENT DOCUMENTS 3,224,259 12/1965 DeNicola ........................ 73/860 X
4,537,080 8/1985 Christiansen .......................... 73/857

OTHER PUBLICATIONS

Sketch of Instron grip with connecting sleeve having a flange.
Istron Corporation single page brochure, bearing number 15, on Modular Actuators, publication date is unknown.

Primary Examiner—Jerry W. Myracle
Attorney, Agent, or Firm—Kinney & Lange

[57] ABSTRACT

A specimen grip for a test specimen that has an actuator for operating the grip remotely mounted and coupled to the grip through a tubular housing which provides for temperature isolation between the grip and the actuator. The grip is specifically adapted to be used in environmental chambers where the grip must operate in either high or low temperatures which can have an effect on the hydraulic actuator used in the grip and connected devices, such as load sensors. By maintaining the actuator on the exterior of the environmental chamber by having a pair of modules that are connected by a sectional connector, a grip can be installed through small ports in the environmental chamber. Once installed, the assembly permits viable operation because the actuator is temperature isolated from the chamber.

8 Claims, 4 Drawing Sheets

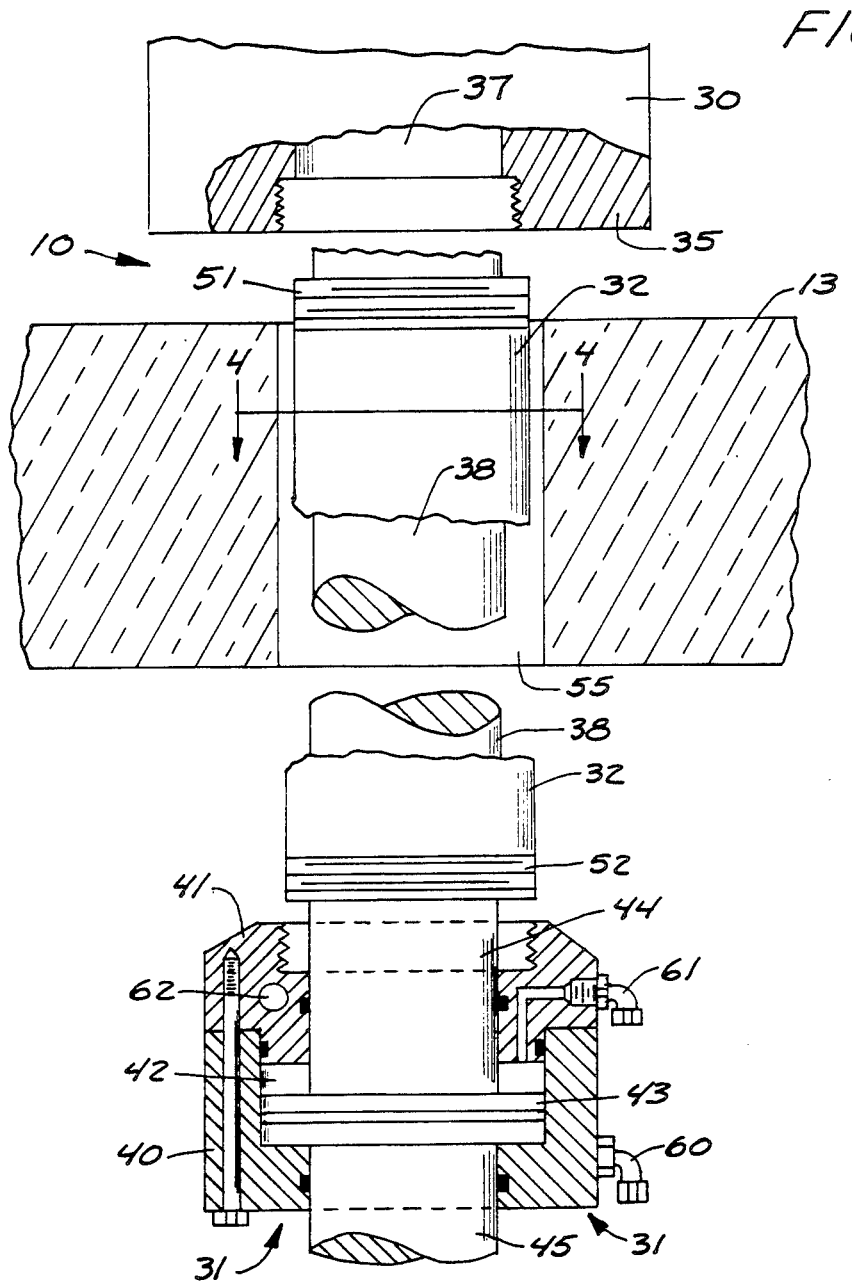
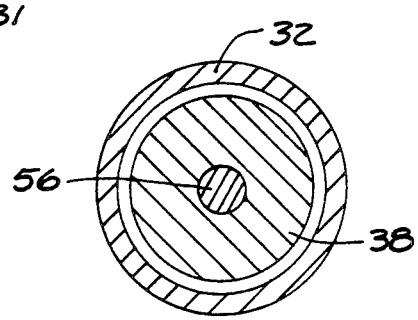

SPECIMEN GRIP WITH REMOTE ACTUATION

BACKGROUND OF THE INVENTION

The present invention relates to the gripping of material specimens for axial tension and/or compression loading of the specimen in an environmental chamber which has the actuator for the grip on the exterior of the chamber to temperature isolate the actuator from the environment of the grip and specimen.

The measurement of the physical properties of material specimens in high or low temperature environment is a well established requirement in the field of materials testing. An environmental chamber is provided to surround the specimen to be tested in either a high temperature or low temperature atmosphere, for simulating conditions that are required for the testing. These conditions can include vacuum or corrosive gases, as well as heat and cold. Generally, passively activated grips have been used in environmental chambers, but actively actuated grips such as those shown in U.S. Pat. No. 4,537,080 are desirable. Actively actuated grips not only are easy to control through remote hydraulic actuation, but they are convenient for loading and unloading of the specimens, they provide accurate alignment of the specimen in the grip, and the grip can be preloaded to permit tension and compression axial loading of the specimen. The actuators can either be a gas or hydraulic oil. The actuator itself does not operate well within the temperature extremes of an environmental chamber.

Thus, a modular actuator that can be used with several different testing grips and which can be installed through a relatively small port in a wall of an environmental chamber to permit actuation of a grip on the inside of the chamber from an actuator on the outside of the chamber is desirable.

Modular actuators have been advanced, in which the actuators can be taken apart and installed. For example, Instron Corporation has provided in continuous tube coupling between an actuator and a specimen grip so the actuator is spaced from the specimen grip, but it is difficult to install, and has couplings that are larger than the main part of the tube coupling so that passing the connectors through the wall of an environmental chamber is difficult. Installation of such grips requires openings that are larger in size than desirable.

SUMMARY OF THE INVENTION

The present invention relates to a grip system for using an active specimen grip within high or low temperature environmental chambers. The activating means or actuator is separated from the grip such that the actuator can be operated in a normal ambient environment substantially unaffected by the temperatures in the environmental chamber, while using conventional grips to permit tension and compression loading, and torsion loading. The grips feature ease of loading of specimens, and general reliable alignment of hydraulic grips. The actuator and grip are connected by a sleeve or tube that is of such size and is constructed so that it can be slipped through a port in a wall of the environmental chamber through an opening that is not substantially larger than the sleeve itself. The grips, acutator and sleeve can be assembled and disassembled easily.

The modular system can be used with direct compression loading grips, tension and compression carrying grips, and by minor modifications used with an axial and torsion loading grip. Low cost, simple operation, and reliable installation and operation is desired.

BRIEF DESCRIPTION OF THE DRAWINGS

FIG. 3 is an exploded schematic view showing the modular construction of a specimen grip for installation in an environmental chamber;

FIG. 4 is a sectional view taken on the line 4—4 in FIG. 3; and

DETAILED DESCRIPTION OF THE PREFERRED EMBODIMENTS

Figure 1:
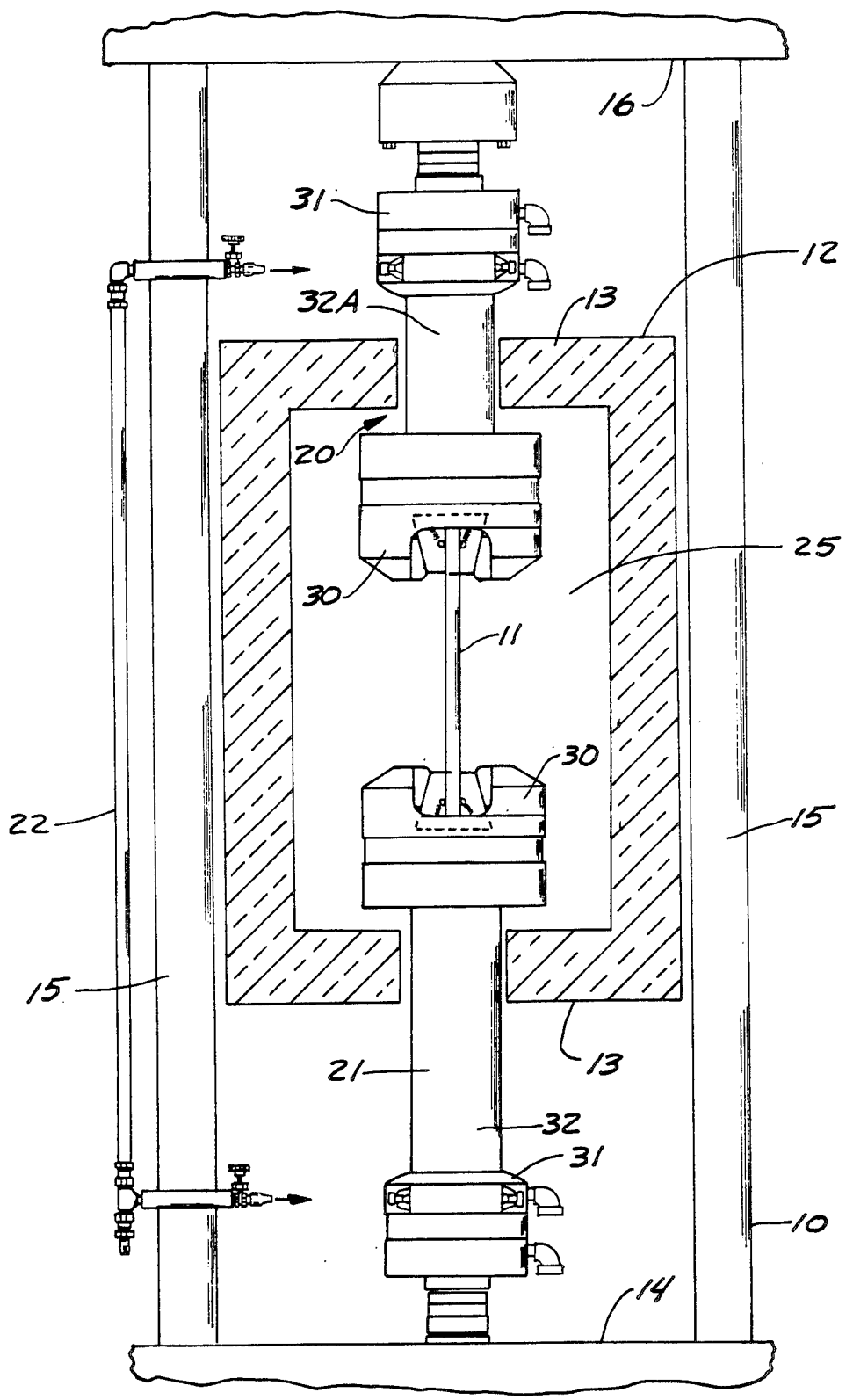
FIG. 1 is a part schematic sectional view of a typical environmental chamber with a specimen gripping system made according to the present invention installed therein.

A load frame indicated generally at 10 is shown schematically, and it is used for loading a specimen also shown schematically at 11, which is mounted on the interior of an environmental chamber 12 that has a pair of end walls 13,13. The chamber 12 is supported relative to the load frame 10 in any desired manner. As shown, the load frame has a base 14, a pair of upright columns 15, and a cross head 16. The cross head supports a modular grip assembly made according to the present invention and illustrated generally at 20 at an upper end of the environmental chamber and also a modular grip assembly illustrated at 21 at a lower end. The grip assemblies are identical, except for the length of a connecting tube between an actuator and the grip members, as will be evident.

A suitable fluid supply line 22 is provided for cooling or warming fluid and can be connected to ports in the grip assemblies as shown.

Figure 2:
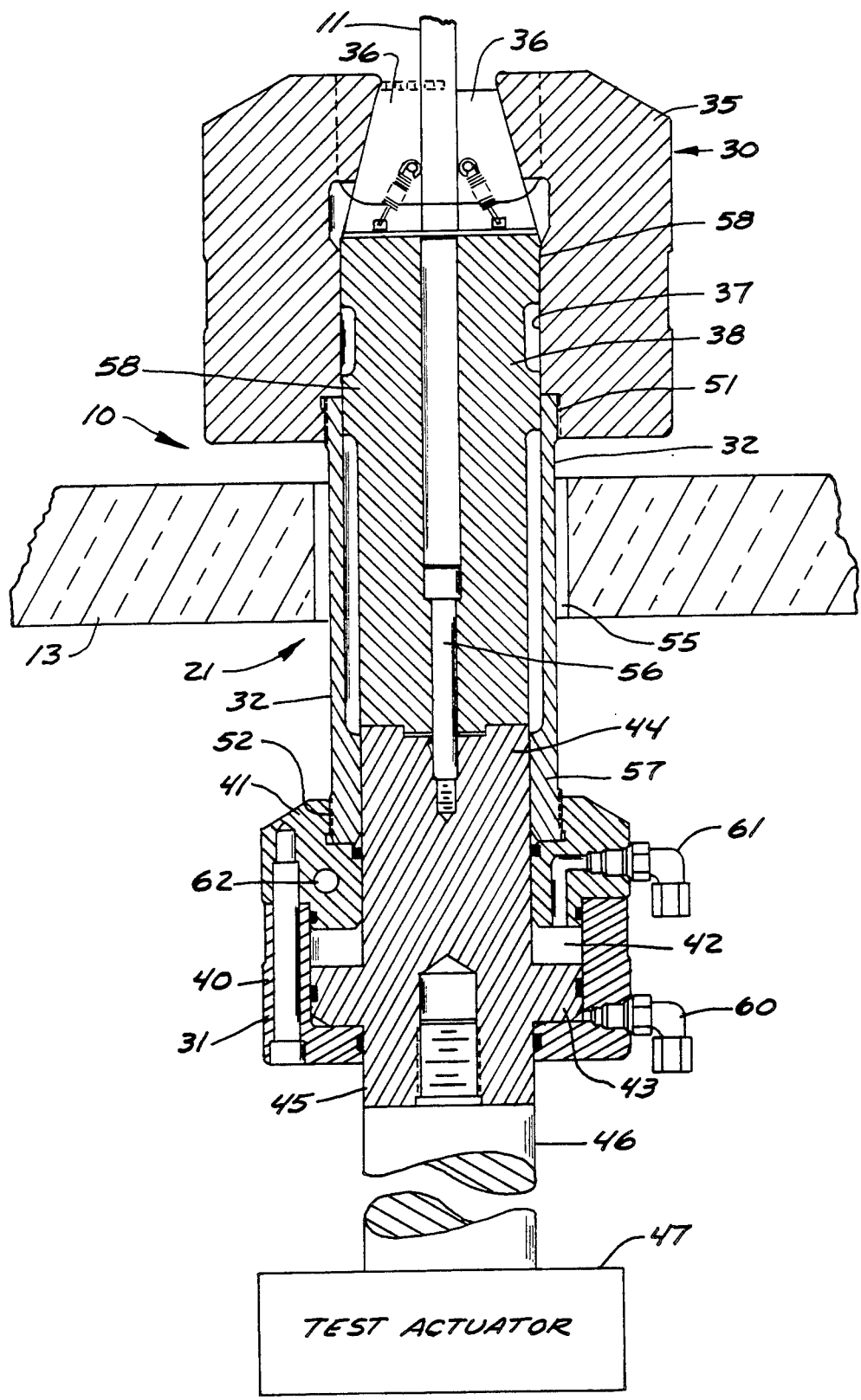
FIG. 2 is a sectional view through a specimen grip made according to the present invention.
Figure 5:
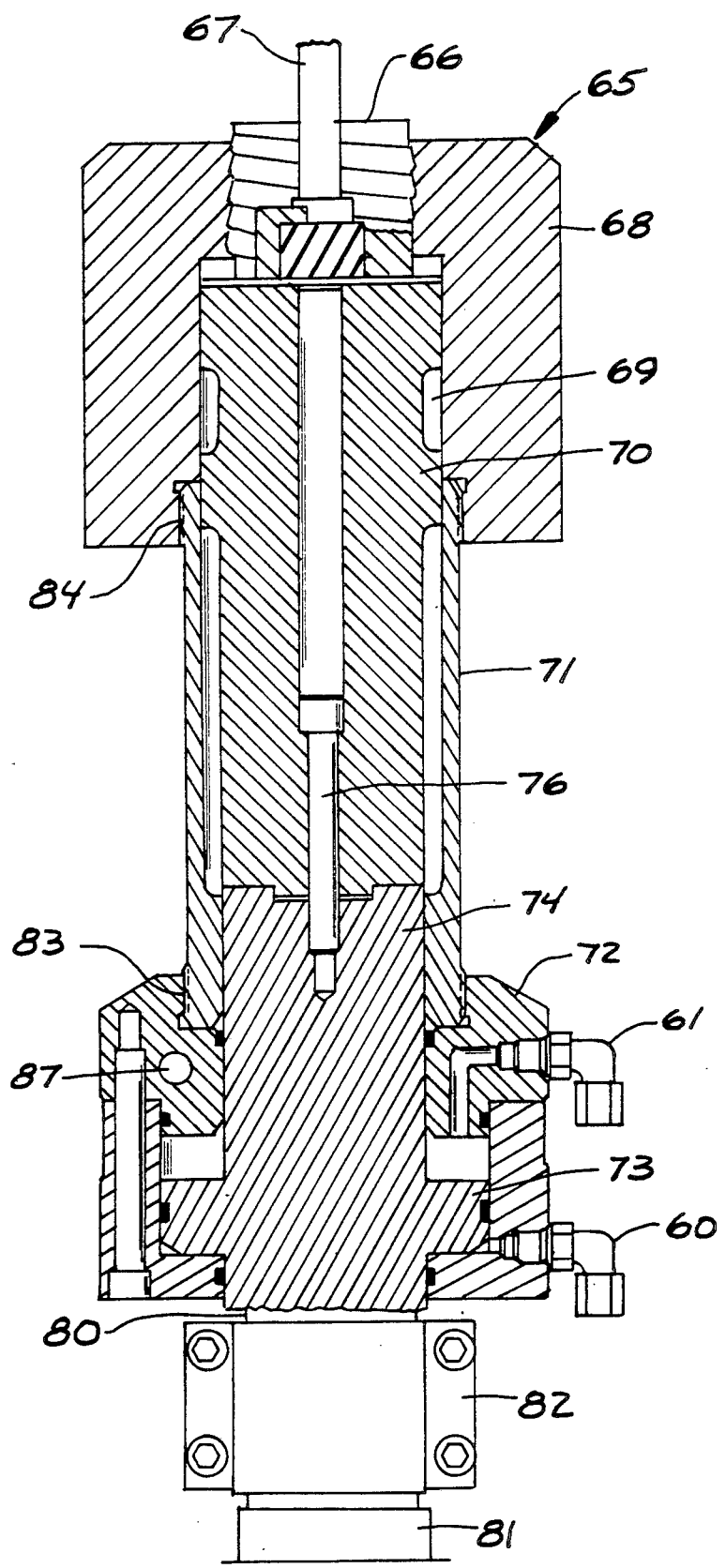
FIG. 5 is a vertical sectional view of a modified device of the present invention illustrating a modified drive for axial and torsion testing utilizing a collet mounting.

The interior chamber 25 of the environmental test chamber 12 is raised to a suitable temperature, or is maintained at a suitable cold temperature for cryogenic testing of the specimen 11, and the grip assemblies 20 and 21 thus have to be capable of operating in this environment. Since it is desirable to have hydraulically actuated grips, accommodating such grips has been difficult because the actuator cylinders are affected adversely by extreme temperatures. As shown, in FIGS. 1 and 2, each of the grip assemblies includes a grip module or member 30, an actuator modular or member 31, and a connecting sleeve or tube 32 and 32A, respectively. The modular grip assembly 21 is shown in FIG. 2 in cross section, and also is shown in an exploded view in FIG. 3. The grip 30 as shown is a wedge lock grip such as that illustrated in U.S. Pat. No. 4,537,080, with the main grip body 35 having an interior cavity with interior wedge surfaces, and wedges 36 in a retracted position that are spaced apart and will receive the specimen 11 therebetween. The grip body 35 in this form has a side opening for loading a specimen and an internal bore 37. An extension piston rod 38 is mounted in bore 37 for slidable movement. The extension piston 38 applies compression loads against the bases of the wedges 36 and when actuated will force the wedges against the interior wedge surfaces of the grip housing, forcing them in toward the center line to tighten down onto the specimen in a conventional manner, with all of the advantages of such grip described in the prior art.

The modular actuator assembly 31 in the form shown is a hydraulic cylinder that has an outer cylinder body section 40, with an actuator end cap 41 held thereon to form an internal chamber 42 in which a piston 43 and integral rod 44 are mounted. The piston 43 has an integral second rod portion 45 extending out through an opening in the base of the cylinder body 40. Rod 45 is connected through suitable connections, such as a threaded connection, to a rod 46 of a test hydraulic actuator 47 that is mounted in the base of the load frame. The actuator 47 can be a reciprocating test actuator, or can be just a tension test actuator, as desired.

The grip 30 and the actuator 31 form modules that are connected together with a third module comprising the connecting sleeve or extension cylinder 32. In the form shown, the extension piston rod or actuator rod 38 is connected to the piston rod 44 with a suitable cap screw 56, and is selected in length with respect to the extension cylinder or sleeve 43 so that the piston will have adequate room for operation and tightening the wedges 36 against the specimen. The modular extension cylinder 32 has a threaded end 51 that threads into a provided threaded bore in the grip body 35, and has a second threaded end 52 that threads into a provided bore in the actuator cap 41, to space the grip 30 from the actuator 31 a desired amount, and to also permit assembly of the modular components on opposite sides of the base wall 13 of an environmental chamber.

The extension cylinder or sleeve 32 can be passed through an opening 55 in wall 13. It can be seen that the port or opening 55 is very close in diameter to the outside diameter of the sleeve 32. The opening that has to be formed in the environmental chamber to accommodate the present device is substantially smaller than that which would be necessary if the grip was to be passed through such an opening, making loss of the atmosphere from the interior of the environmental chamber to the exterior less likely, and also making sealing easier if seals are necessary.

As shown, the piston rod 44 will be suitably guided in a throat section 57 of the cylinder or sleeve 32 and the rod 44 also has a pair of land or guide sections 58 at the grip end that are closely slidably guided on the interior bore 37 of the grip body 35.

As shown in FIG. 3, the lower sleeve threaded section 52 and the upper sleeve threaded section 51 can both be disassembled from the modules, prior to installation of the actuator 31 and the grip 30, so that the assembled piston rod 44, and rod extension 38, can be slid into the sleeve 32 and passed through the port or opening 55 in the chamber wall. Then, the grip 30 can be threaded onto the end 51 of the sleeve 32 from the interior of the environmental chamber. The end cap of actuator 31 is threaded onto the threads 52 from the exterior of the environmental chamber, so that assembly is quick and complete, and the bore 55 is maintained at a small size that is substantially smaller than either the grip or the actuator diameters.

Once the module parts are threaded together, hydraulic fluid under pressure is provided to a fitting 60 to pressurize chamber 42 below the base end of the piston 43. This forces the actuator housing, sleeve 32 and grip 65 housing down against the wedges 36 to clamp the wedges tightly in place at a desired pressure. A fitting 61 is used for return fluid.

Additionally, fluid ports indicated at 62 are provided in the actuator end cap for flow through of fluid, to aid in maintaining the actuator and connecting devices, such as load sensors, at moderate temperatures. The need for temperature moderation is substantially reduced because of the remote location of the actuator outside of the environmental chamber. The assembly permits the advantages of hydraulic grip actuation to be usable with environmental chambers.

In a modified form of the invention, a grip 65 is made to provide for a clamping in a collet 66 for holding flat specimens such as that shown at 67 in a conventional manner. Collets for holding threaded specimens or the like also may be provided. The collet can be any desired form for the test sample that is being run. The grip 65 has a grip body 68 that has an internal bore 69 in which an extension piston rod 70 is slidably mounted, in the same manner as previously explained. An actuator 72 of substantially the same design as that previously described has an internal piston 73 inside an internal bore, and piston 73 carries a piston rod 74 that is joined to the extension rod 70 utilizing a suitable cap screw 76. The collet is preloaded by applying pressure through fitting 60 to the actuator. In this form of the invention, enough preload between the collet, extension piston rod 70 and piston rod 74 permits torsional loading of the specimen. Because with the collet mounting, the test specimen can be placed in tension and also in torsion by twisting the actuator and piston rod when loading. In this form of the invention, a lower rod section 80 is joined to an actuator rod 81 (connected to a conventional test torsion tension actuator) utilizing a threaded coupling 82 that operates in the manner described in U.S. Pat. No. 4,809,556. The coupling 82 is threaded at opposite ends with different hand threads. The coupling is tightened down circumferentially to clamp the two rod parts 80 and 81 tightly together without backlash in the joint as explained in the aforementioned patent.

The torque from the actuator used for torsion testing will be transmitted primarily through the piston rod. This torque is transmitted by friction between wedges 36, extension piston rod 38 and integral rod 44. The outer sleeve and grip housing will be carried along with the rod.

Additional collets or other test specimen carriers can be adapted as well. The sleeve or cylinder extension 71, grip 65 and actuator 72 again form a modular assembly because of thread sections 83 at the actuator end, and 84 at the grip end, so that the unit can be broken down into modules and then assembled through the port or opening in a base wall of an environmental chamber. Either the grip or the actuator can be assembled to cylinder extension 71 prior to placing the extension 71 through the opening in the environmental chamber.

A cooling fluid port 87 is provided in the actuator 72 in the same manner as previously explained, and this provides for a cooling fluid to be passed through the actuator to maintain the temperature at a level substantially equal to the ambient temperature, and form a heat block for heat conducted by the cylindrical sleeve 71.

It should be noted that the coupling 82, is designed to provide a backlash free connection between the piston 73 and piston rod 74 and the actuator rod 71. Load is carried to the collet, in the case of FIG. 4, and to the wedges, directly through the center load carrying rods to provide positive actuation.

Again, different types of actuators can be used, such as pneumatic cylinders or electric drive actuators, as well as the hydraulic actuators shown. The actuator is maintained remote from the grip and the connecting sleeve is smaller size than the grip housing. When the grip housing is removed, the remaining end portion at the grip end of the connecting sleeve is no larger than the part of the sleeve or connecting cylinder which fits through the opening in the chamber wall.

The materials used for the actuator can be conventional, as can the seals, because the operation is in tolerable temperatures. The sleeve and grip modules are made of non-corrosive, high temperature materials such as suitable stainless steel.

Although the present invention has been described with reference to preferred embodiments, workers skilled in the art will recognize that changes may be made in form and detail without departing from the spirit and scope of the invention.

What is claimed is:

1. An active specimen grip assembly for use in loading of a material specimen comprising:
   a specimen grip assembly having an outer grip housing with a transverse dimension;
   separate actuator means for actuating said specimen grip assembly to grip a specimen to be tested;
   a tubular connecting sleeve having a maximum transverse dimension smaller than a maximum transverse dimension of said outer grip housing; and
   means for connecting the sleeve to the outer grip housing and for permitting removal of said outer grip housing from said sleeve, the means for connecting having a maximum transverse dimension which is not substantially larger than the maximum transverse dimension of the sleeve.

2. The active specimen grip assembly of claim 1 wherein said sleeve is threaded to a portion of the outer grip housing to form the means for connecting, and wherein said sleeve is a generally circular cross-section cylindrical tube.

3. The active grip specimen assembly according to claim 1, and means for removably coupling the actuator to the sleeve, said sleeve being of length to pass through the wall of a desired environmental test chamber to position the actuator means on an opposite side of the wall from the specimen grip assembly.

4. The active grip specimen assembly of claim 1 wherein the separate actuator means comprises a hydraulic actuator having a piston and piston rod, and connection means for connecting a reciprocating actuator to one end of the piston rod, said connection means comprising a back lash free connection means, the piston rod having a second portion extending toward the grip, an extension piston rod connected to the second piston rod portion, and torque transmitting means between said second piston rod portion and said extension piston rod for permitting transferring torque loads through the extension piston rod to the grip.

5. A modular actuator assembly for use with an environmental chamber having a port of a first diameter through a wall thereof, said environmental chamber having an environment different from ambient conditions, comprising:
   a specimen grip member for mounting inside said environmental chamber and for loading a specimen in the chamber;
   an actuator assembly for operating the specimen grip to grip a specimen, said actuator assembly being positioned to the exterior of said environmental chamber;
   an operating link extending between said actuator assembly and said specimen grip assembly for operating the specimen grip; and
   a tubular connecting sleeve joining the specimen grip member and the actuator, corresponding in length to the operating link, said tubular sleeve passing through said port and surrounding said operating link, said tubular sleeve being substantially smaller in diameter than the specimen grip member and removably coupled to the specimen grip member on the interior of the environmental chamber.

6. The modular actuator assembly of claim 5 and threadable connection means between the tubular connecting sleeve and the specimen grip member to form a removable coupling between the specimen grip member and the tubular sleeve.

7. The modular actuator assembly of claim 6 and threadable connection means for coupling the actuator assembly to the tubular sleeve.

8. The modular actuator assembly of claim 5 and port means in said actuator assembly for carrying fluid to moderate temperature effects in the actuator assembly.

* * * * *